(12) United States Patent
Takei

(10) Patent No.: US 8,662,370 B2
(45) Date of Patent: Mar. 4, 2014

(54) INTRODUCER SYSTEM AND ASSEMBLY FOR SURGICAL STAPLERS

(76) Inventor: Hidehisa Thomas Takei, Riverside, CA (US)

( * ) Notice: Subject to any disclaimer, the term of this patent is extended or adjusted under 35 U.S.C. 154(b) by 337 days.

(21) Appl. No.: 12/756,713

(22) Filed: Apr. 8, 2010

(65) Prior Publication Data

US 2011/0248067 A1    Oct. 13, 2011

(51) Int. Cl.
*A61B 17/10*  (2006.01)
*A61B 17/04*  (2006.01)

(52) U.S. Cl.
USPC .................................................. 227/179.1

(58) Field of Classification Search
USPC ............................................ 227/175.1–182.1
See application file for complete search history.

(56) References Cited

U.S. PATENT DOCUMENTS

| | | | | |
|---|---|---|---|---|
| 1,119,290 A * | 12/1914 | Lachman | ...................... | 81/436 |
| 1,747,647 A * | 2/1930 | Racicot | .......................... | 81/436 |
| 2,007,626 A | 7/1935 | Waring | | |
| 3,433,225 A * | 3/1969 | Voss et al. | ....................... | 604/14 |
| 3,672,367 A | 6/1972 | Scislowicz | | |
| 4,471,782 A | 9/1984 | Shuffield | | |
| 5,314,436 A | 5/1994 | Wilk | | |
| 5,346,115 A * | 9/1994 | Perouse et al. | .............. | 227/179.1 |
| 5,355,897 A | 10/1994 | Pietrafitta et al. | | |
| 5,389,067 A * | 2/1995 | Rejai | ............................. | 604/14 |
| 5,404,870 A * | 4/1995 | Brinkerhoff et al. | ......... | 600/184 |
| 5,437,628 A * | 8/1995 | Fox et al. | ......................... | 604/14 |
| 5,486,183 A * | 1/1996 | Middleman et al. | .......... | 606/127 |
| 5,562,678 A * | 10/1996 | Booker | .......................... | 606/113 |
| 5,669,918 A * | 9/1997 | Balazs et al. | ................... | 606/139 |
| 5,836,503 A | 11/1998 | Ehrenfels et al. | | |
| 5,944,728 A * | 8/1999 | Bates | ............................... | 606/127 |
| 6,036,720 A * | 3/2000 | Abrams et al. | ................. | 606/213 |
| 6,159,220 A * | 12/2000 | Gobron et al. | ................. | 606/127 |
| 6,174,318 B1 * | 1/2001 | Bates et al. | ...................... | 606/127 |
| 7,318,830 B2 | 1/2008 | Mayoral | | |
| 7,559,934 B2 * | 7/2009 | Teague et al. | .................. | 606/113 |
| 7,842,068 B2 * | 11/2010 | Ginn | ............................... | 606/213 |
| 7,867,249 B2 * | 1/2011 | Palermo et al. | ................ | 606/213 |
| 7,874,981 B2 * | 1/2011 | Whitman et al. | .............. | 600/184 |
| 7,901,416 B2 * | 3/2011 | Nolan et al. | .................... | 606/153 |
| 7,905,900 B2 * | 3/2011 | Palermo et al. | ................ | 606/213 |
| D650,075 S * | 12/2011 | Anglay et al. | ................ | D24/133 |
| 8,070,759 B2 * | 12/2011 | Stefanchik et al. | ............ | 606/139 |
| 8,109,962 B2 * | 2/2012 | Pal | ................................ | 606/200 |
| 2001/0041899 A1 * | 11/2001 | Foster | ............................ | 606/127 |
| 2003/0225419 A1 * | 12/2003 | Lippitt et al. | ................... | 606/127 |
| 2005/0165438 A1 | 7/2005 | Gritsus | | |
| 2005/0187576 A1 * | 8/2005 | Whitman et al. | .............. | 606/219 |

(Continued)

*Primary Examiner* — Robert Long
(74) *Attorney, Agent, or Firm* — McCarter & English, LLP

(57) ABSTRACT

An introducer assembly for use with a surgical stapler is provided. The introducer assembly includes an elongated main body portion, one or more mounting mechanisms associated with the main body portion, and a plurality of petals or fingers positioned at a distal end of the elongated main body portion. The one or more mounting mechanisms are adapted to detachably mount with respect to the surgical stapler. The plurality of petals or fingers define a distal junction and a proximally-directed mounting member that is adapted to detachably engage a distal portion of the surgical stapler. The plurality of petals or fingers define an inner region that accommodates a distal end of the surgical stapler. The distal junction and the proximally-directed mounting member associated with the plurality of petals or fingers are adapted to disengage upon application of a requisite proximally-directed force to the elongated body portion. Methods and combinations that utilize the introducer are also disclosed.

15 Claims, 5 Drawing Sheets

(56) References Cited

U.S. PATENT DOCUMENTS

| | | | |
|---|---|---|---|
| 2005/0236459 A1* | 10/2005 | Gresham | 227/175.1 |
| 2006/0287674 A1* | 12/2006 | Ginn et al. | 606/221 |
| 2007/0051375 A1* | 3/2007 | Milliman | 128/856 |
| 2010/0163598 A1* | 7/2010 | Belzer | 227/181.1 |
| 2011/0114697 A1* | 5/2011 | Baxter et al. | 227/175.1 |
| 2011/0114698 A1* | 5/2011 | Baxter et al. | 227/175.1 |
| 2011/0114699 A1* | 5/2011 | Baxter et al. | 227/175.1 |
| 2011/0114700 A1* | 5/2011 | Baxter et al. | 227/179.1 |
| 2011/0118761 A1* | 5/2011 | Baxter et al. | 606/148 |

\* cited by examiner

INTRODUCER SYSTEM AND ASSEMBLY FOR SURGICAL STAPLERS

BACKGROUND

1. Technical Field

The present disclosure is directed to a system/assembly for facilitating introduction and/or positioning of a surgical stapler at or to a desired anatomical location. More particularly, the present disclosure is directed to an introducer system/assembly that is adapted to be detachably mounted with respect to a surgical stapler, e.g., an end-to-end or end-to-side anastomotic stapler.

2. Background Art

Wound closure techniques include the use of surgical staplers and clip appliers in many clinical applications. Surgical staplers and clip appliers take many forms and are adapted for use in various modalities. Thus, for example, certain staplers are specifically designed for application of skin staples, while others are adapted for use in internal procedures. Indeed, surgical staplers and clip appliers have been developed and are employed in both "open" and "minimally invasive" surgical procedures.

One particular form of surgical stapler having a specialized design and specialized uses is a circular stapler for use in performing end-to-end and end-to-side anastomotic procedures, e.g., the EEA™ line of staplers (Covidien, Inc., Mansfield, Mass.). The noted circular staplers generally take the form of a tubular instrument that defines a tubular shaft at a distal end thereof. A disposable cartridge is generally adapted to be mounted with respect to tubular shaft, such cartridge containing two or more circular rows of staggered staples, pushers for driving the staples from the cartridge and a circular knife within the inner ring of staples. An anvil assembly is adapted to mount with respect to a distally extending rod such that, when the anvil assembly is brought into close juxtaposition with the staple cartridge, the staples may be discharged from the cartridge and formed against anvil pockets defined in the anvil assembly. In addition, the anvil assembly also generally includes a plastic ring into which the circular knife is driven during the stapling operation. A control mechanism is provided at the proximal end of the surgical stapler to control relative movement between the staple cartridge and the anvil assembly. Once approximated, an actuating mechanism at the proximal end of the surgical stapler is employed to deliver staples into tissue and advance the circular knife into the plastic ring, thereby forming an anastomotic junction.

Circular staplers of the type described above are generally employed in esophageal and rectal procedures, although the staplers have utility throughout the gastrointestinal tract. For example, in bowel surgeries, purse-stringed bowel segments to be anastomosed are passed over the anvil assembly—which is typically dome-shaped—and the staple cartridge, respectively, and the purse-strings tightened around the central shaft. The anvil assembly and staple cartridge are then approximated and upon actuation of the actuating mechanism, an instantaneous, minimally-inverting, end-to-end or end-to-side anastomosis is effectuated. The circular stapler may be introduced and positioned through a natural orifice, e.g., the anus (e.g., a low anterior resection of the rectum) or the mouth (e.g., high esophago-gastric anastomosis). Alternatively, the circular stapler can be introduced through an opening formed during a procedure, e.g., in the stomach for esophagogastrostomy, in the small bowel for esophagojejunostomy, the terminal ileum for esophagocecostomy, and the like.

Of note, introduction and positioning of a circular stapler can be difficult in practice due to the physical structures associated with the distal end of the stapler. In particular, the stapler cartridge generally defines a substantially flat surface that is to be advanced through the intestinal tract or other anatomical lumen. Indeed, challenges exist in introducing a substantially flat surface into an orifice and thereafter advancing such flat surface through the lumen, e.g., up into the rectum, potentially encountering redundancies to the colon, redundant mucosa and/or prominent valves. Difficulties in introducing a surgical stapler and/or positioning the surgical stapler in a desired anatomical location can inhibit its successful use.

Prior art efforts to address the above-noted issues have been less than satisfactory. Thus, for example, U.S. Pat. No. 5,404,870 to Brinkerhoff et al., U.S. Pat. No. 5,836,503 to Ehrenfels et al., and U.S. Patent Publication No. 2005/0165438 to Gritsus disclose devices and/or geometries that are intended to facilitate introduction and/or positioning of surgical staplers. Additional patent-related publications of background interest include U.S. Pat. Nos. 7,318,830; 5,355,897; 5,314,436; 4,471,782; 3,672,367; and 2,007,626, as well as U.S. Patent Publication No. 2005/0236459.

However, despite efforts to date, a need remains for introducer systems and assemblies that facilitate introduction and positioning of a surgical stapler relative to a desired anatomical location. A need further remains for introducer systems and assemblies that are adapted for easy and reliable detachment from the surgical stapler once its introduction and/or positioning functionalities are complete. These and other needs are satisfied by the introducer systems and assemblies disclosed herein.

SUMMARY

According to the present disclosure, an advantageous device, assembly and method are provided for facilitating introduction and/or positioning of a surgical stapler relative to a desired anatomical location. The disclosed device/assembly takes the form of a "tear-away" introducer that is adapted to be detachably mounted with respect to the surgical stapler. In exemplary embodiments, the disclosed introducer includes a distal component that defines a plurality "petals" or "fingers" that (i) come together in a mounting member at their distal end, and (ii) cooperate with an elongated body portion at their proximal end. The petals/fingers define an inner region that is configured and dimensioned to accommodate the distal end of a surgical stapler, thereby facilitating anatomical introduction of the circular stapler. The elongated main body portion of the disclosed introducer defines mounting mechanism(s), e.g., "C-shaped" mounting brackets, that are adapted to detachably engage the outer surface/shaft of the surgical stapler.

In an exemplary embodiment, the disclosed introducer is generally mounted with respect to a surgical stapler with the distal mounting member positioned relative to a distal component of the surgical stapler. The mounting mechanisms, e.g., C-shaped brackets of the introducer, detachably engage the stapler shaft. In advancing the surgical stapler to the desired stapling site, the petals/fingers of the introducer help to guide the stapler past potential obstructions and/or anatomical irregularities. Thereafter, the introducer is adapted to be detached from the stapler by pulling proximally on the elongated body portion, causing the petals/fingers to "tear away" from around the distal portion of the surgical stapler, thereby facilitating removal from the stapler.

In an alternative embodiment, the disclosed introducer may include or cooperate with one or more intermediate structures, e.g., extension member(s). For example, one or more intermediate structures may be positioned between the disclosed petals/fingers and the elongated body portion. Of note, the intermediate structure(s) may include structural features and/or functionalities that facilitate interaction with a surgical stapler, e.g., mounting mechanism(s) for detachably securing the disclosed introducer with respect to a surgical stapler.

Additional features, functions and benefits of the disclosed introducer device/assembly will be apparent from the figures which follow, particularly when viewed in conjunction with the accompanying description.

BRIEF DESCRIPTION OF THE FIGURES

To assist those of ordinary skill in the art in making and using the introducer device and assembly of the present disclosure, reference is made to the accompanying figures, wherein.

DESCRIPTION OF EXEMPLARY EMBODIMENT(S)

The disclosed devices, assemblies and methods advantageously facilitate introduction and/or positioning of a surgical stapler relative to a desired anatomical location. In addition, the disclosed devices, assemblies and methods permit a user to remotely detach the device/assembly from the surgical stapler, thereby permitting unobstructed operation of the surgical stapler in a desired manner. The disclosed devices, assemblies and methods also permit a user to extend the shaft of the surgical stapler, thereby permitting the surgical stapler to reach anatomical locations that otherwise may be hard to reach, while facilitating the introduction and/or positioning of the surgical stapler to these locations. The disclosed devices, assemblies and methods have wide ranging applicability and utility, including specifically applications throughout the gastrointestinal tract.

Figure 1:
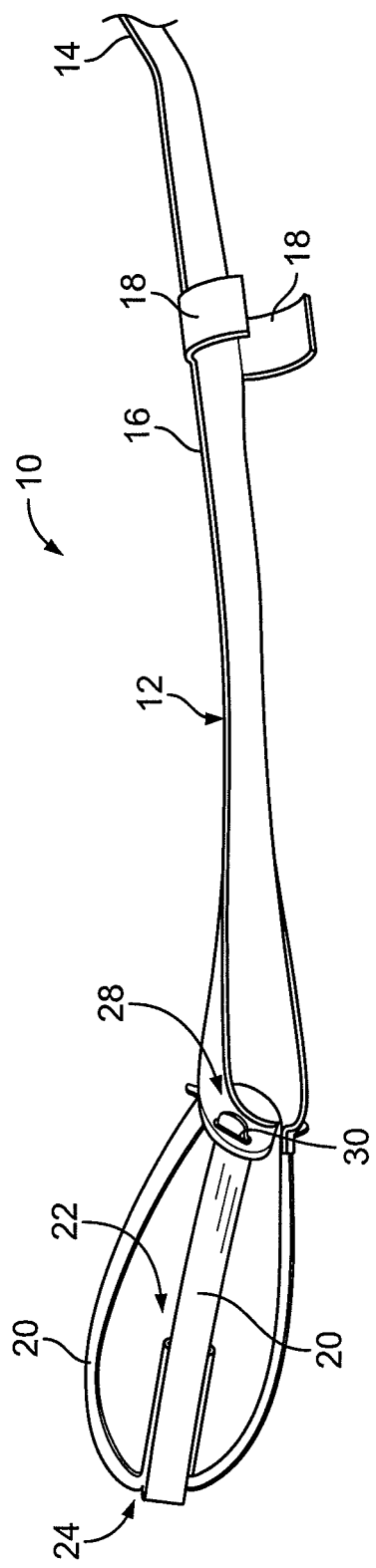
FIG. 1 is a perspective view of an exemplary introducer assembly according to the present disclosure.
Figure 2:
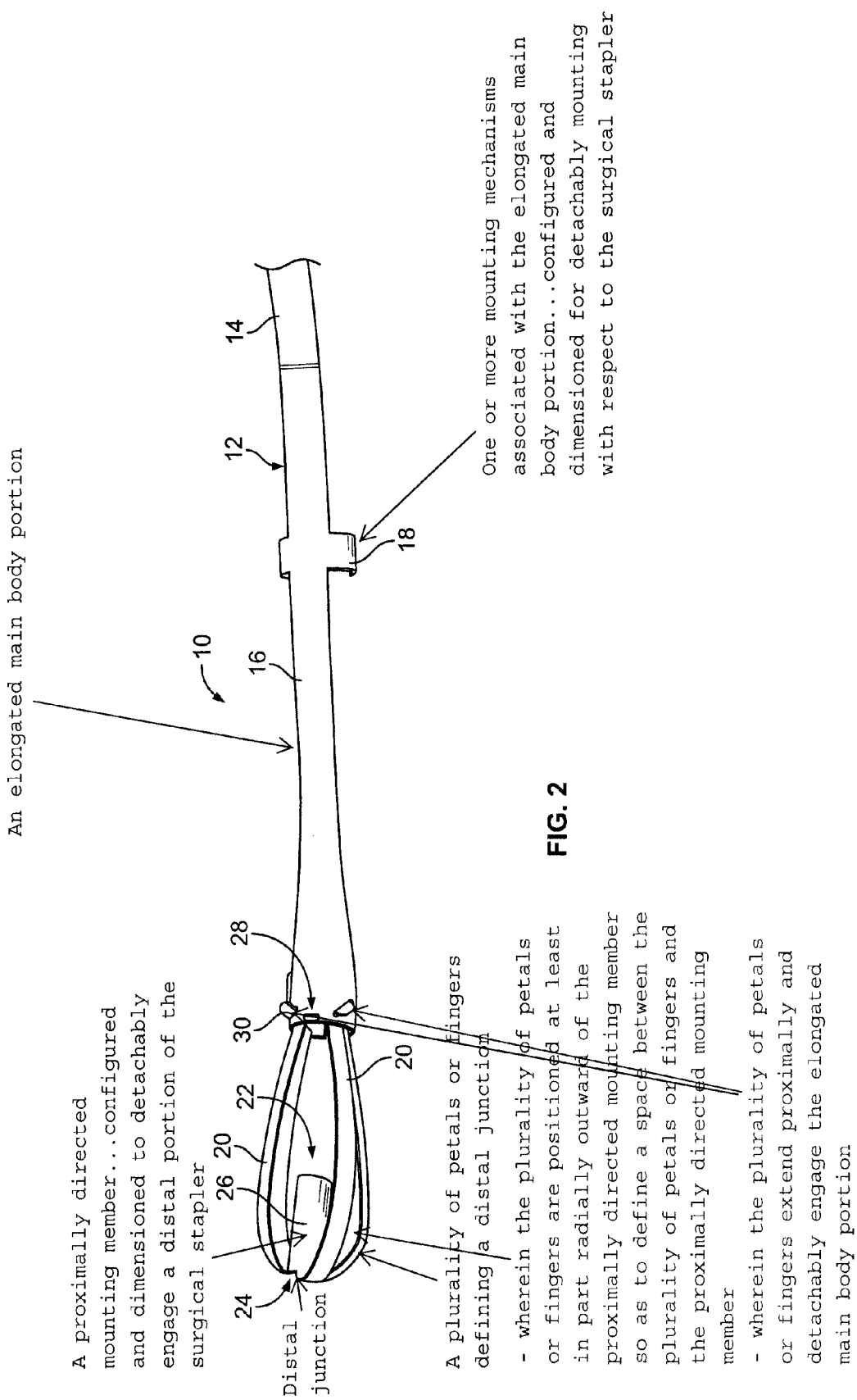
FIG. 2 is a further perspective view of an exemplary introducer assembly according to the present disclosure, rotated approximately 180° relative to the view of FIG. 1.

With initial reference to FIGS. 1 and 2, an exemplary introducer 10 is schematically depicted. Introducer 10 includes an elongated body member 12 that defines a proximal extension arm 14 that is angularly oriented relative to main body portion 16. The functionality of proximal extension arm 14 will be described in greater detail herein below with reference to FIGS. 3 and 4. The main body portion 16 defines a substantially arcuate geometry that, in use, is adapted to cooperate with a substantially cylindrical surgical stapler. In exemplary embodiments of the present disclosure, the main body portion 16 defines an arcuate body region that extends over an arc of about 120° to about 180°, although alternative arcuate dimensions may be employed. Indeed, the arcuate geometry of the disclosed main body portion 16 is generally selected so as to achieve two principal objectives: (i) cooperate/engage with the outer face of a cylindrical surgical stapler during stapler introduction/positioning, and (ii) permit remote detachment of the introducer from the surgical stapler, as desired by a user. Provided the foregoing principal objectives are satisfied, the arcuate geometry of the disclosed main body portion 16 may vary as to arcuate extent, radius of curvature and the like.

One or more mounting mechanisms are generally provided along the length of the main body portion 16 of the introducer 10 to facilitate detachable mounting of introducer 10 relative to a surgical stapler. Thus, in the exemplary embodiment of FIGS. 1 and 2, a pair of opposed, substantially C-shaped brackets 18 extend from main body portion 16 at an intermediate location at an intermediate location. The C-shaped brackets 18 generally exhibit sufficient flexibility/resilience to facilitate positioning around a substantially cylindrical shaft of a surgical stapler, yet sufficient strength/rigidity to ensure that introducer 10 is securely retained on or with respect to the surgical stapler until detachment is desired. In preferred embodiments of the present disclosure, the mounting mechanism(s), e.g., C-shaped brackets 18, are integrally formed with main body portion 16, e.g., as a single molded unit. However, the present disclosure also encompasses designs/implementations wherein the mounting mechanism(s) are separately formed/fabricated and joined to the main body portion 16, e.g., through sonic welding, adhesive, pin/slot, bayonet lock or other joining technology. In addition, although only a single pair of brackets 18 are depicted with respect to the exemplary introducer 10 of FIGS. 1 and 2, it should be understood that the present disclosure is not limited to such implementation, and that additional mounting brackets (or other mounting mechanisms) may be positioned along the length extent of the main body portion 16 without departing from the spirit or scope of the present disclosure.

With further reference to FIGS. 1 and 2, exemplary introducer 10 includes a plurality of petals or fingers 20 that extend from the distal end of main body portion 16. In the exemplary embodiment of FIGS. 1 and 2, introducer 10 includes four (4) petals/fingers 20, but the present disclosure is not limited by or to such exemplary implementation. Thus, as used herein, the term "plurality" of petals/fingers encompasses any design that includes two or more petals/fingers that deliver the functionalities described herein. In particular, petals/fingers 20 define an inner region 22 that is configured/dimensioned to accommodate the distal end of a surgical stapler, including specifically the staple cartridge of a surgical stapler. In addition, petals/fingers 20 are substantially joined at a distal junction 24 and, from such distal junction 24, define a proximally-directed mounting member 26.

In an alternative embodiment, the disclosed introducer 10 may include or cooperate with one or more intermediate structures, e.g., extension member(s) (not pictured). For example, one or more intermediate structures may be positioned between the disclosed petals/fingers 20 and the main body portion 16, e.g., such that the petals/fingers 20 are mounted with respect to the intermediate structure(s). Of note, the intermediate structure(s) may include structural features and/or functionalities that facilitate interaction with a surgical stapler, e.g., mounting mechanism(s) for detachably securing the disclosed introducer with respect to a surgical stapler.

In exemplary embodiments of the present disclosure, mounting member 26 defines a central channel that is configured and dimensioned to receive a distally-directed shaft member extending from the surgical stapler. Alternatively, mounting member 26 may define a rod-like structure that is configured and dimensioned for receipt in a distally-directed channel associated with the surgical stapler. In any case, mounting member 26 is adapted to detachably secure the distal end of introducer 10 with respect to the distal end of a surgical stapler. Various techniques may be employed to combine the plurality of petals/fingers 20 at distal junction 24 and to define mounting member 26 therefrom. For example, the petals/fingers 20 may be adhered with respect to each other using conventional adhesives. Alternatively, one or more banding members may be positioned around the petals/fingers 20 in the vicinity of distal junction 24 and/or the proximally-directed mounting member 26. Additionally, the plurality of petals may be mounted with respect to the main body portion by way of intermediate structure(s), e.g., for purposes of reaching anatomical locations that may otherwise be difficult to reach.

Petals/fingers 20 are also joined to main body portion 16 at proximal junction region 28. In the exemplary embodiment of FIGS. 1 and 2, proximal junction region 28 includes circumferentially spaced mounting slots 30 formed toward the distal end of main body portion 16. Indeed, as shown in FIGS. 1 and 2, main body portion 16 flares to a greater arcuate extent at its distal end, thereby accommodating four (4) circumferentially spaced mounting slots for petals/fingers 20. Thus, according to the exemplary implementation of FIGS. 1 and 2, petals/fingers 20 are fed through the mounting slots 30 and anchored therewithin. Additional steps may be taken to ensure that the petals/fingers 20 do not disengage from main body portion 16, e.g., application of an adhesive or the like. Of note, the petals/fingers 20 are generally fabricated from a material that exhibits greater flexibility than main body portion 16. Although plastics are preferred, it is contemplated that appropriate metals may be employed in fabricating introducer 10, as will be apparent to persons of skill in the art.

Thus, the disclosed introducer 10 exhibits "tear-away" functionality in that, once the mounting member 26 is mounted with respect to the distal end of a surgical stapler, a proximally-directed force applied to main body portion 16, e.g., by grasping proximal extension arm 14, will overcome the banding of the petals/fingers 20 at distal junction and in the region of mounting member 26. In this way, the plurality of petals/fingers 20 become disengaged from each other and from the distal end of the surgical stapler. Once disengaged from each other and from the surgical stapler, the petals/fingers 20 are free to slide proximally along the exterior of the surgical stapler. In addition, application of a proximally-directed force to the main body portion 16, e.g., to proximal extension arm 14, is generally effective to disengage the mounting mechanism(s) associated with the main body portion 16, e.g., C-shaped brackets 18, from the surgical stapler.

Figure 3:
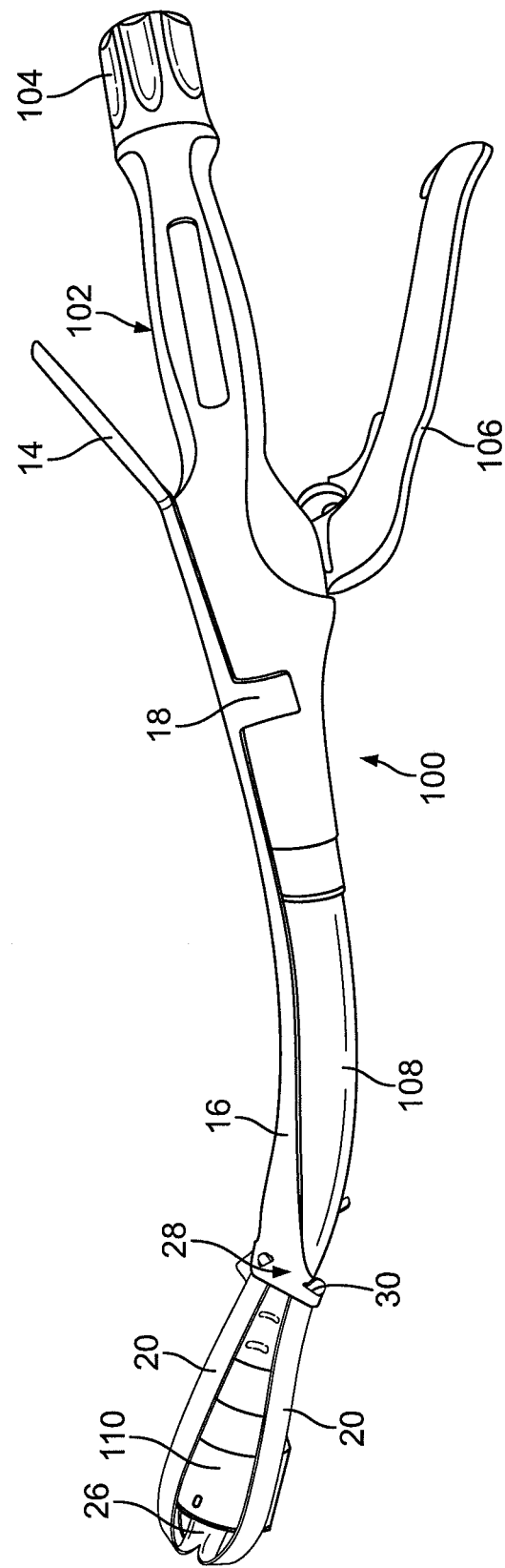
FIG. 3 is a perspective view of the exemplary introducer assembly of FIGS. 1 and 2 mounted with respect to an exemplary surgical stapler.
Figure 4:
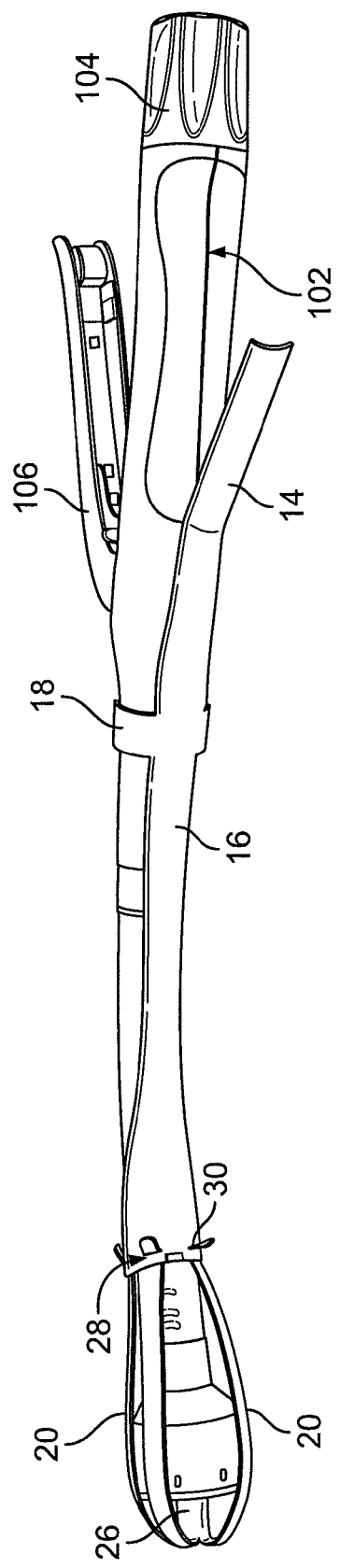
FIG. 4 is a further perspective view of an exemplary introducer assembly mounted with respect to an exemplary surgical stapler, rotated by approximately 90° relative to FIG. 3.
Figure 5:
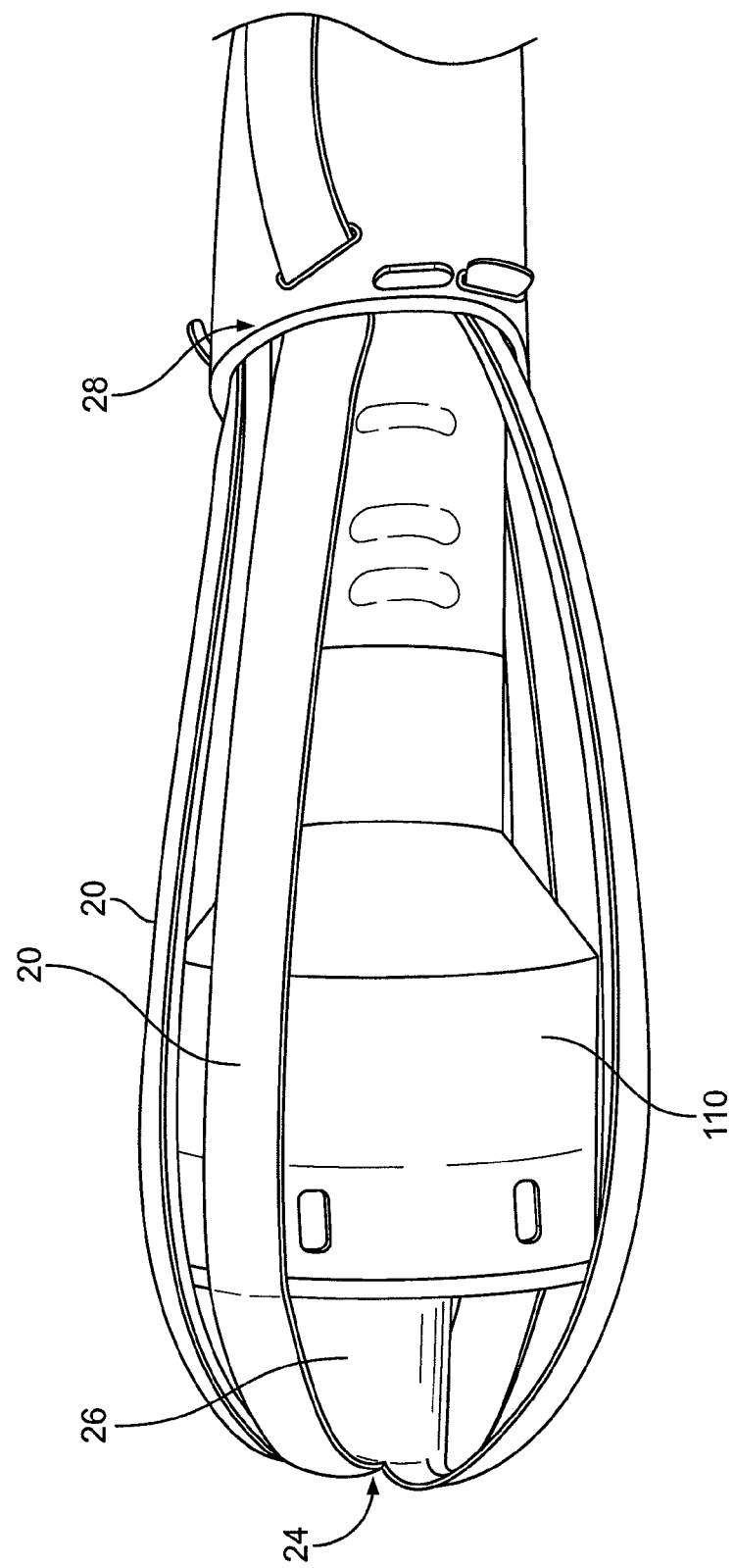
FIG. 5 is an enlarged view of the distal region of an exemplary introducer assembly according to the present disclosure mounted with respect to a surgical stapler.

Turning to FIGS. 3-5, the exemplary introducer 10 of FIGS. 1 and 2 is detachably mounted with respect to a conventional surgical stapler according to an illustrative implementation of the present disclosure. Thus, as shown in FIGS. 3 and 4, conventional surgical stapler 100 includes a handle 102 that includes an approximating knob 104 and an actuating trigger 106. A curved shaft 108 extends from handle 102 and cooperates with a staple cartridge 110 positioned at a distal end thereof. Although surgical stapler 100 is illustrative of the types of surgical staplers with which the disclosed introducer device/assembly/method may be employed, it is neither exclusive nor limiting of the potential applications and/or uses of the disclosed introducer.

As shown in FIGS. 3 and 4, introducer 10 is detachably mounted with respect to stapler 100 in three ways: (i) the arcuate geometry of main body portion 16 substantially conforms to the geometry of shaft 108; (ii) C-shaped brackets 18 engage stapler 100 in a substantially cylindrical region of handle 102; and (iii) mounting member 26 detachably engages a distally-facing cooperating structure associated with staple cartridge 110 (see FIG. 5). Thus, in use the disclosed introducer 10 is generally detachably mounted with respect to a surgical stapler, e.g., surgical stapler 100. The petals/fingers 20 surround the distal end of surgical stapler 100, particularly the substantially flat face of staple cartridge 110, thereby providing a substantially flexible and tapered guide geometry (when viewed from the distal end of the stapler/introducer assembly) that assists in introducing and navigating surgical stapler 100 to a desired anatomical location. In particular, in advancing the surgical stapler 100 to a desired stapling site, the petals/fingers 20 of the introducer 10 help to guide the stapler 100 past potential obstructions and/or anatomical irregularities.

Once surgical stapler 100 is brought to a desired anatomical location, the user can easily disengage introducer 10 from surgical stapler 100 and withdraw the introducer from the surgical field. In particular, the user disengages introducer 10 from surgical stapler 100 by pulling proximally on main body portion 16 of introducer 10, e.g., by grasping proximal extension arm 14, thereby disengaging mounting member 26 from the stapler cartridge 110, disengaging C-shaped brackets 18 from handle 102, and disengaging the arcuate main body portion 16 overall from the surgical stapler shaft 108. Thus, in toto, the disclosed petals/fingers 20 function to "tear away" from the staple cartridge 110 so as to permit withdrawal from the surgical field. Of note, the angled geometry of proximal extension arm 14 facilitates ready access to and grasping thereof by a user when disengagement of introducer 10 from stapler 100 is desired.

The disclosed introducer offers significant advantages for introducing and positioning surgical staplers in a desired anatomical location. In addition, the disclosed introducer is designed such that modifications to conventional surgical staplers are unnecessary to gain the clinical benefits associated therewith. Indeed, the disclosed introducer is susceptible to widespread adoption and use, thereby overcoming a fundamental issue encountered in many surgical applications, namely reliable introduction and positioning of the surgical stapler despite potential irregularities and/or anomalies in a patient's anatomy.

Although the present disclosure has been described with reference to exemplary embodiments and implementations thereof, it is to be understood that the present disclosure is not limited by or to such exemplary embodiments and/or implementations. Rather, the present disclosure is susceptible to various modifications, variations and/or enhancements without departing from the spirit and/or scope of the present disclosure. Thus, the present disclosure expressly encompasses such potential modifications, variations and/or enhancements, as will become apparent to persons of skill in the art from the present disclosure.

The invention claimed is:

1. An introducer assembly for use with a surgical stapler, comprising:
 a. an elongated main body portion;
 b. one or more mounting mechanisms connected with respect to the elongated main body portion, said one or more mounting mechanisms being configured and dimensioned for detachably mounting with respect to the surgical stapler;
 c. a plurality of petals or fingers defining a distal junction and a mounting member that extends proximally relative to the distal junction and is configured and dimensioned to detachably engage a distal portion of the surgical stapler, wherein the plurality of petals or fingers are positioned at least in part radially outward of the proximally extending mounting member so as to define a space between the plurality of petals or fingers and the proximally extending mounting member; and wherein the plurality of petals or fingers extend proximally relative to the distal junction and detachably engage the elongated main body portion.

2. The introducer assembly of claim 1, wherein the elongated main body portion defines a proximal extension arm that is angled with respect to a distal extent of the elongated main body portion.

3. The introducer assembly of claim 1, wherein the elongated main body portion defines a substantially arcuate geometry.

4. The introducer assembly of claim 3, wherein the substantially arcuate geometry extends over an arc of about 120° to about 180°.

5. The introducer assembly of claim 1, wherein the elongated main body portion flares out to define a junction region, and wherein the plurality of petals or fingers are detachably engaged to the elongated main body portion in the junction region.

6. The introducer assembly of claim 5, wherein the junction region includes a plurality of circumferentially spaced slots through which the plurality of petals or fingers are joined.

7. The introducer assembly of claim 1, wherein the plurality of petals or fingers define an inner region that is configured and dimensioned to accommodate a distal end of the surgical stapler.

8. The introducer assembly of claim 1, wherein the plurality of petals or fingers are detachably joined with respect to each other at the distal junction.

9. The introducer assembly of claim 1, wherein the proximally-extending mounting member defines either (i) a central channel for receipt of a distally-directed shaft member extending from the surgical stapler, or (ii) a rod-like structure for receipt in a distally-directed channel associated with the surgical stapler.

10. The introducer assembly of claim 1, wherein the distal junction and the proximally-extending mounting member associated with the plurality of petals or fingers are adapted to disengage upon application of a requisite proximally-directed force to the elongated main body portion.

11. In combination:
a. a surgical stapler that includes a handle, a shaft and a distally positioned stapling member;
b. an introducer assembly including (i) an elongated main body portion, (ii) one or more mounting mechanisms connected with respect to the elongated main body portion; and (iii) a plurality of petals or fingers positioned at a distal end of the elongated main body portion;

wherein said one or more mounting mechanisms are detachably mounted with respect to the surgical stapler, wherein said plurality of petals or fingers define a distal junction and a mounting member that extends proximally relative to the distal junction and are detachably engaged with respect to a distal portion of the surgical stapler, and wherein the plurality of petals or fingers are positioned at least in part radially outward of the proximally extending mounting member so as to define a space between the plurality of petals or fingers and the proximally extending mounting member, and wherein the plurality of petals or fingers extend proximally relative to the distal junction and detachably engage the elongated main body portion.

12. The combination of claim 11, wherein the plurality of petals or fingers associated with the introducer define an inner region that is configured and dimensioned to accommodate a distal end of the surgical stapler.

13. The combination of claim 11, wherein the plurality of petals or fingers are detachably joined with respect to each other at the distal junction.

14. The combination of claim 11, wherein the proximally-extending mounting member defines either (i) a central channel for receipt of a distally-directed shaft member extending from the surgical stapler, or (ii) a rod-like structure for receipt in a distally-directed channel associated with the surgical stapler.

15. The combination of claim 11, wherein the distal junction and the proximally-extending mounting member associated with the plurality of petals or fingers are adapted to disengage upon application of a requisite proximally-extending force to the elongated main body portion.

* * * * *